United States Patent
Sakamoto et al.

(10) Patent No.: US 6,280,931 B1
(45) Date of Patent: *Aug. 28, 2001

(54) METHOD FOR SPECIFICALLY AMPLIFYING A DYSTROGLYCAN, α-SARCOGLYCAN, OR ENDOTHELIN BRECEPTOR CDNA OF AN EXTREMELY SMALL

(75) Inventors: Aiji Sakamoto; Fumio Hanaoka, both of Saitama (JP)

(73) Assignee: The Institute of Physical and Chemical Research, Saitama (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/910,864

(22) Filed: Aug. 13, 1997

(30) Foreign Application Priority Data

Aug. 16, 1996 (JP) .................................. 8-216506

(51) Int. Cl.⁷ .............................. C12Q 1/68; C12P 19/34
(52) U.S. Cl. ................................. 435/6; 435/91.2
(58) Field of Search ................. 435/6, 91.2, 810

(56) References Cited

U.S. PATENT DOCUMENTS 5,057,410  10/1991  Kawasaki et al.
5,618,717 * 4/1997  Wei et al. ........................ 435/325

FOREIGN PATENT DOCUMENTS 2 260 811      4/1993  (GB).
WO 93 18176    9/1993  (WO).

OTHER PUBLICATIONS

Datta et al., J. Clin. Oncol. 12(3), 475–482, 1994.*
Cooper et al., Ann. Med. 26, 9–14 (1994).*
Naylor et al., Lancet 337, 635–639 (1991).*
Chelly et al., Proc. Natl. Acad. Sci. USA 86, 2617–2621 (1989).*
Chelly et al., Biochem. Biophys. Res. Comm. 178(2), 553–557 (1991).*
Bertling W.M. et al., "Determination of 5'Ends of Specific MRNAS by DNA Ligase–Dependent Amplification" *PCR Methods Applications*, vol. 3, No. 2, Oct. 1, 1993, pp. 95–99.
Leister, et al. Trends in Genetics (1996) vol. (12)(1) p. 11.*
Rosa, et a (1996) Biochem Biophys Res Comm. vol. 223 p272–277.*
Nelson (1996) Cancer Research vol. 56 p 663–668 (1996, Feb. 15).*
Duggan, et al (1996) Journal of Neurological Sciences vol. 140 p. 30–39.*

* cited by examiner

*Primary Examiner*—Kenneth R. Horlick
(74) *Attorney, Agent, or Firm*—Fish & Richardson P.C.

(57) ABSTRACT

The invention provides a method for selectively amplifying a cDNA synthesized from an mRNA expressed only in an extremely small quantity. The method comprises synthesizing a cDNA from a target mRNA using an oligonucleotide primer complementary to at least a part of the 3' untranslated region of the mRNA and amplifying the resultant cDNA using a 5' primer and a 3' primer which is located 5' upstream of the oligonucleotide primer for synthesizing a cDNA.

12 Claims, 3 Drawing Sheets

METHOD FOR SPECIFICALLY AMPLIFYING A DYSTROGLYCAN, α-SARCOGLYCAN, OR ENDOTHELIN BRECEPTOR CDNA OF AN EXTREMELY SMALL

BACKGROUND OF THE INVENTION

1. Field of the Invention

The present invention relates to a method for selectively amplifying a cDNA. More specifically, the invention is concerned with a method for selectively amplifying a cDNA synthesized from an mRNA expressed only in an extremely small quantity.

2. Prior Art

Inherited diseases, cancers and some types of progeria and dementia are caused by occurrence of variation in specific genes. Thus, these diseases are often called generically "genetic diseases". In these genetic diseases, abnormal characters appear only in such an organ or tissue where a specific gene involved in the disease is expressed. However, the variation in the gene itself is present in any tissue in the body. Therefore, as a technique for diagnosing a genetic disease, a method may be considered which comprises extracting genomic DNA from leukocytes in peripheral blood that is most easy to sample and then amplifying the genomic DNA.

As a method for amplifying genomic DNA, firstly, a method by PCR (polymerase chain reaction) may be given. Then, a genetic disease is diagnosed by searching the amplified DNA for variation in the base sequence.

However, it is difficult in general to amplify an entire genomic DNA by performing PCR just one time because the size of genomic DNA is too big.

As a means to amplify genomic DNA, secondly, a method of amplifying exons alone may be given because variation in bases involved in a genetic disease only occurs in the region of "exons" encoding proteins. In order to amplify exons alone, information on genetic structure, i.e. information as to which regions of the genomic DNA are exons is necessary.

However, it is seldom that such information has been previously known.

Due to these reasons, in many cases it is necessary to use as a sample for genetic diagnosis not peripheral blood but a sample obtained by biopsy from a tissue manifesting symptoms. Generally, mRNA (precursors of proteins) is extracted from the tissue sample obtained and cDNA is synthesized therefrom. Subsequently, a PCR is performed (this method is called "RT-PCR").

However, biopsy gives a great pain to a patient and, moreover, some tissues such as brain are extremely difficult to perform biopsy.

For the reasons described above, it is the present situation that genetic diagnosis using easy-to-sample blood has many restrictions, and that many restrictions are also present in the case of examining a tissue obtained by biopsy to find out at which part of the coding region of a candidate causative gene of an inherited disease or the like variation in specific base sequences has occurred.

On the other hand, recently, it has been made clear by RT-PCR or the like that such a gene that is expressed only tissue-specifically (e.g., in brain or heart) is actually expressed in an extremely small quantity in leukocytes in peripheral blood, fibroblasts in skin and the like (Chelly, J. et al., Proc. Natl. Acad. Sci. USA 86, 2617–2621 (1989)). It is appropriate to interpret this phrase "expressed in an extremely small quantity" that inhibition of gene expression in the body is not 100% complete but there is some "leakage", rather than to interpret this as physiological gene expression. In other words, the "expressed in an extremely small quantity" does not mean that a specific gene is expressed naturally and properly though in an extremely small quantity. It is appropriate to interpret that an mRNA being expressed in a specific tissue such as brain may leak out of the tissue though it should be expressed only in that specific tissue, and that since the body cannot inhibit the leakage of such mRNA completely, the mRNA which has leaked out in an extremely small quantity exists in tissues other than the specific tissue as well (e.g., peripheral blood leukocyte).

Such RNA which has thus leaked out is called "leaky RNA" or "illegitimate transcription". If a target cDNA can be amplified selectively from such "leaky" mRNA by RT-PCR, it is believed that, in principle, diagnosis of any genetic disease can become possible by examining peripheral blood.

In conventional RT-PCR, total RNA is extracted from a tissue and then mRNAs are isolated and purified. Thereafter, using oligo(dT) primers or random primers, a pool of cDNAs from mRNAs being expressed in the tissue is prepared (Michael A. Innis et al., PCR Protocols: A Guide to Methods and Applications, Academic Press Inc. (1990)). Then, a PCR is performed using an appropriate set of oligo DNA primers specific to a target cDNA.

Since the template for the above PCR is a mixture of cDNAs from the entire tissue, contamination with (mixing of) a large number of non-specific amplified products may occur when the amount of cDNAs or the number of PCR cycles is increased. Accordingly, it has been difficult to apply this method to the "illegitimate transcription" described above.

OBJECTS AND SUMMARY OF THE INVENTION

It is the object of the present invention to provide a method for specifically amplifying a cDNA, in particular, a cDNA synthesized from an mRNA expressed only in an extremely small quantity.

As a result of extensive and intensive researches toward the solution of the above assignment, the present inventors have found that it is possible to selectively amplify a cDNA from an mRNA expressed only in an extremely small quantity by locating a 3' primer for cDNA amplification at 5' upstream to that of a primer for cDNA synthesis from the mRNA. Thus, the present invention has been achieved.

The present invention relates to a method for selectively amplifying a cDNA of an extremely small quantity, comprising synthesis of a cDNA from a target mRNA using an oligonucleotide primer complementary to at least a part of the 3' untranslated region of the mRNA; and amplification of the resultant cDNA using a 5' primer and a 3' primer which is located upstream of the oligonucleotide primer for synthesis of a cDNA.

As examples of the cDNA, a cDNA encoding dystroglycan, α-sarcoglycan or endothelin B receptor may be given.

The distance between the primer for cDNA synthesis and the 3' primer for cDNA amplification is preferably 1 kb or less, more preferably in the range from 1 to 300 bp. As the 5' primer and the 3' primer for cDNA amplification, primers located adjacent to the coding region of the target mRNA in the upstream and the downstream thereof, respectively, may be used.

BRIEF DESCRIPTION OF THE DRAWINGS

FIG. 1 represents a primer; 1' represents another primer; 2 represents contaminant RNA; 3 represents contaminant cDNA; 4 represents 5' primer; and 5 represents 3' primer.

PREFERRED EMBODIMENTS OF THE INVENTION

Hereinbelow, the present invention will be described in more detail.

The method of the invention for amplifying a cDNA of an extremely small quantity is characterized by synthesizing a cDNA from a target mRNA by hybridizing a primer for reverse transcription to the 3' untranslated region of the mRNA and amplifying the resultant cDNA using a 5' primer and a 3' primer which is located at 5' upstream to that of the primer for reverse transcription.

First, an mRNA which is the target of amplification is prepared from an individual tissue. This tissue is not particularly limited. For example, blood, brain, heart, muscle, or the like may be used. Preferably, blood is used in view of easy sampling. Alternatively, a commercially available mRNA (e.g., from Clonetech) may be used.

In the present invention, those mRNAs which are expressed tissue-specifically and are difficult to isolate from the tissue by biopsy or the like may be enumerated particularly as a target mRNA for amplification. Such mRNAs are reverse-transcribed to cDNAs and then amplified. Specific examples of such cDNAs include a cDNA encoding human dystroglycan (hDG) involved in progressive muscular dystrophy, a cDNA encoding human α-sarcoglycan (hα-SG) involved in another progressive muscular dystrophy, and a cDNA encoding human endothelin B receptor (hET$_B$) involved in Hirschsprung's disease. Since the above proteins are expressed in specific tissues (e.g., hDG and hET$_B$ are expressed in brain and heart), the mRNAs encoding those proteins leak out into peripheral blood leukocytes in only extremely small quantities. Therefore, the method of amplification of the present invention is particularly useful in amplifying such mRNAs. However, the target of amplification of the present invention is not limited to the mRNAs and cDNAs described above.

Preparation of mRNA may be performed by any of the known techniques. For example, the guanidinium method (Chirgwin, J. J. et al., Biochemistry 18:5294 (1979)), AGPC method (Chomoczynski, P. and Sacchi, N., Anal. Biochem., 162:156–159 (1987)) and the like may be used.

In one embodiment of the present invention, mRNA is prepared using "ISOGEN-LS" kit from Nippon Gene. When this kit is used, fractionation of leukocytes is unnecessary and mRNA is obtained as a part of total RNA. However, it is not necessary to isolate and purify mRNA alone. Alternatively, a commercially available mRNA (e.g., poly (A)$^+$ RNA from Clonetech) may be used to start cDNA synthesis directly.

Figure 1A:
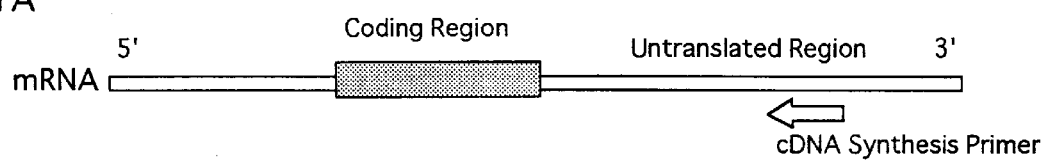
FIGS. 1A–1C show a summary of the method of amplification according to the present invention.
Figure 1B:
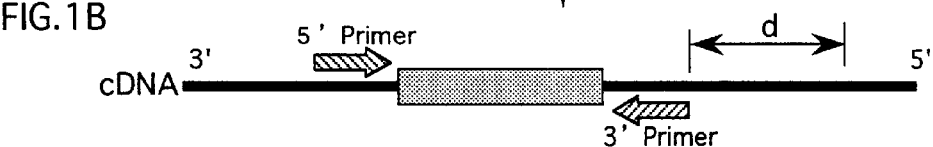

Subsequently, cDNA is synthesized from the mRNA prepared above (see FIG. 1B). As a primer for cDNA synthesis, an oligonucleotide complementary to at least a part of the 3' untranslated region of a target mRNA molecule may be used (see FIG. 1A). This primer is synthesized based on the base sequence of the mRNA molecule. Since it is the object of the present invention to synthesize a cDNA from an mRNA of which the sequence is known and to amplify the resultant cDNA, a sequence of any region of the target mRNA can be selected in designing the above primer. Subsequently, the primer of interest can be obtained by chemical synthesis in a DNA synthesizer from, for example, Applied Biosystems Inc. The length of this primer is usually 20–30 bases, preferably 24–26 bases.

A cDNA synthesis reaction is performed with a reverse transcriptase (e.g., Super Script II RNaseH$^-$ Reverse Transcriptase from GIBCO BRL).

When cDNA is synthesized conventionally using oligo (dT) primers, unwanted cDNA molecules are also synthesized. However, when a primer specific to a target mRNA molecule is used for cDNA synthesis as in the present invention, the cDNA template to be used in the subsequent amplification can be made extremely specific to a target cDNA.

Figure 1C:
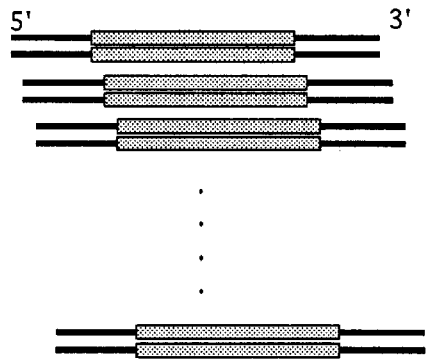

Subsequently, the cDNA obtained as described above is amplified (see FIG. 1C). Amplification may be performed by any of the known techniques. For example, polymerase chain reaction (PCR) may be used.

Primers for PCR may be synthesized in the same manner as described above for the synthesis of the cDNA synthesis primer. The length of PCR primers is usually 20–40 bases, preferably 25–35 bases.

The 3' primer for PCR is located 5' upstream of the cDNA synthesis primer. That is, the 3' primer for PCR is located between the '3 end of the coding region (open reading frame) and the site of the cDNA synthesis primer on the cDNA to be amplified (FIGS. 1A and B). The distance between the 3' primer for PCR and the cDNA synthesis primer (shown as "d" in FIG. 1B) is not particularly limited unless the two primers are overlapped even partially. Usually, this distance is preferably 1 kb or less, more preferably in the range from 1 to 300 bp.

In the present invention, the locations of the PCR primers are not particularly limited. Preferably, they are designed so that they are located as immediately as possible adjacent to the coding region (FIG. 1B). The term "adjacent to" used herein means not only that the 5' primer and the '3 primer are located immediately upstream (i.e., 1 bp upstream) and immediately downstream (i.e., 1 bp downstream) of the coding region, respectively, but it also means that they may be located away from the coding region up to about 300 bp. For example, suppose a cDNA fragment has a 300 bp base sequence in which the coding region is located from positions 101 to 200. The 5' primer may be designed so that it is located, for example, from positions 76 to 100 (1 bp upstream of coding region) or from positions 41 to 75 (25 bp upstream of the coding region); and the 3' primer may be designed so that it is located, for example, from positions 201 to 220 (1 bp downstream of the coding region) or from positions 210 to 234 (10 bp downstream of the coding region). Then, by performing the so-called "Long PCR" using LA Taq (Takara) or the like, it is possible to amplify the entire coding region of the target cDNA through a PCR of just one time.

If the 3' primer for PCR is identical to the cDNA synthesis primer, the following inconveniences will arise. Briefly, even if a cDNA specific to a target mRNA has been synthesized, non-specific cDNAs mixed in the reaction solution might possibly be amplified.

Figure 2:
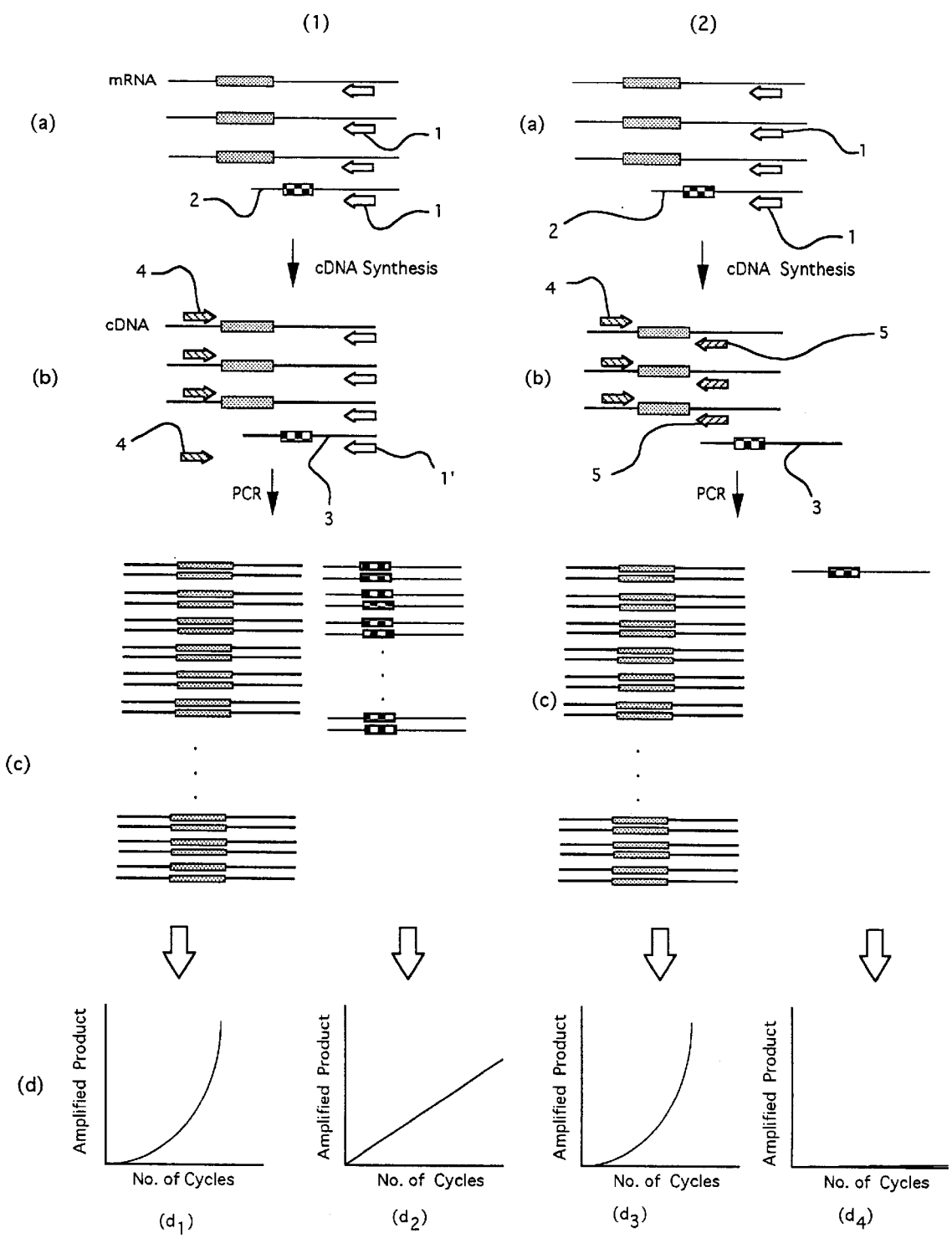
FIG. 2 shows a summary of the method of amplification according to the present invention. In this

For example, as shown in FIG. 2, when an identical 3' primer (primer 1 in FIG. 2 (1)(a)) is used for both reverse transcription and PCR, if a non-target mRNA (contaminant RNA 2 in FIG. 2 (1)(a)) which can accidentally hybridize to the reverse transcription primer is mixed at the stage of reverse transcription, contaminant cDNA 3 is also synthesized from contaminant RNA 2 by reverse transcription (FIG. 2 (1)(b)). Accordingly, in the subsequent amplification process, linear functional amplification of contaminant cDNA 3 inevitably occurs (see (c) and ($d_2$) in FIG. 2 (1)) because the 3' primer (primer 1' in FIG. 2 (1)(b)) can hybridize to the site of the reverse transcription primer on contaminant cDNA 3, even though this cDNA does not hybridize to the 5' primer for PCR (primer 4 in FIG. 2 (1)(b)).

On the other hand, as shown in FIG. 2 (2), when the 3' primer for PCR (primer 5 in FIG. 2 (2)(b)) is located at 5' upstream to that of the reverse transcription primer (primer 1 in FIG. 2 (2)(a)), even if primer 1 has accidentally hybridized to contaminant mRNA 2 to synthesize contaminant cDNA 3 at the stage of reverse transcription (FIG. 2 (2)(b)), the probability that primer 5 hybridizes to contaminant cDNA 3 in the subsequent amplification process will be extremely small. In other words, the cDNA to be irrelevantly amplified by this PCR should accidentally hybridizes to all of the reverse transcription primer (primer 1), the 3' primer for PCR (primer 5) and the 5' primer for PCR (primer 4). Such a probability is believed to be extremely small.

Consequently, according to the method of the invention, non-specific amplified products will not be produced even when the amount of the cDNA template or the number of PCR cycles has been increased (FIG. 2 (2)($d_4$)) and, thus, specific amplification of the target cDNA can be expected (FIG. 2 (2)($d_3$)). This means that the method of the invention is extremely useful for selectively amplifying, in particular, an mRNA expressed only in an extremely small quantity.

Furthermore, according to the present invention, it is not necessary to isolate and purify mRNA from total RNA. Even when rRNA and tRNA are mixed at the stage of reverse transcription, a primer specific to a target mRNA hybridizes to the mRNA alone to thereby enable selective cDNA synthesis.

A PCR is performed after incubation of a specific reaction solution at 94° C. for 2 min and addition of LA Taq (Takara) to the solution using an appropriate PCR reactor (e.g., Thermal Cycler 480 from Perkin Elmer Cetus).

Reaction conditions may be selected as follows, for example.

A reaction is performed for Z cycles (94° C. for 1 min, x ° C. for 1 min and 72° C. for Y min), and finally the reaction solution is incubated at 72° C. for 10 minutes. X, Y and Z vary depending on the target cDNA for amplification and may be determined appropriately. Y is determined on the basis of 1 min per 1 kb of the cDNA fragment to be amplified. X and Z are most appropriately determined in the range from 45 to 70° C. and in the range from 35 to 40 cycles, respectively.

After the completion of the PCR, the amplified product is confirmed by agarose gel electrophoresis. If necessary, the amplified product is recovered from the gel and the base sequence thereof is determined.

By analyzing the thus amplified product, it is possible to detect a mutation involved in a genetic disease. That is, by sequencing the cDNA amplified, it is possible to find out variation in a particular gene (e.g., deletion, replacement, insertion, etc.). If the gene in the patient tested has variation, then the patient is judged to be affected by the disease.

EXAMPLES

Hereinbelow, the present invention will be described more specifically with reference to the following Examples. However, the present invention is not limited to the following Examples in technical scope.

Example 1

Amplification of a cDNA Encoding Human Dystroglycan (hDG) which is One of the Candidate Proteins Involved in Progressive Muscular Dystrophy In this Example, cDNA from peripheral blood was amplified for the purpose of amplifying a cDNA encoding human dystroglycan (hDG) which is one of the candidate proteins involved in progressive muscular dystrophy.

(1) Isolation of RNA from Peripheral Blood

To 1 ml of peripheral blood collected and treated with heparin, 3 ml of ISOGEN-LS (Nippon Gene) was added. Total RNA was prepared according to the manufacturer's instructions and suspended in 10 μl of RNase-free $H_2O$. According to this method, total RNA can be extracted directly without separation of leukocytes from peripheral blood.

From 1 ml of peripheral blood, 60–90 μg of total RNA was extracted.

(2) cDNA Synthesis

The composition of the reaction solution for cDNA synthesis was as follows.

| Aqueous RNA solution | 10 μl |
|---|---|
| Primer for cDNA synthesis | 1 μl |
| (hDGP: SEQ ID NO. 1) (10 mM) | |
| Total | 11 μl |

The primer hDGP (SEQ ID NO. 1) for cDNA synthesis corresponds to positions 3202 to 3226 (located 123 bp downstream of the coding region) of the cDNA sequence shown in SEQ ID NO. 10 encoding dystroglycan (hDG) involved in progressive muscular dystrophy.

The reaction solution described above was incubated at 70° C. for 10 min, then immediately transferred into ice water and left stationary for 2 min to thereby denature RNA. The resultant reaction solution was centrifuged lightly. Then, the following reagents were added thereto and left stationary at room temperature (22° C.) for 10 min to thereby anneal the primer to poly(A)$^+$ RNA.

| 5 × First Strand Buffer (BRL) | 4 μl |
|---|---|
| 0.1 M DTT (BRL) | 2 μl |
| dNTP mix (10 mM each; Pharmacia) | 1 μl |
| NAasin (40 U/μl; Promega) | 1 μl |
| Total | 8 μl |

To the mixture obtained above (19 μl), 1 μl of the reverse transcriptase Super Script II (BRL) was added to make the total volume 20 μl and incubated at 37° C. for 1 hr. 1 μl of 0.5 M EDTA was added to the mixture to terminate the reaction. After ethanol precipitation, the resultant pellet was suspended in 9.5 μl of pure water.

(3) Amplification of the Target cDNA Primers used for amplification were as follows.

5' primer hDGU: SEQ ID NO. 2

3' primer hDGL: SEQ ID NO. 3

The 5' primer corresponds to positions 294 to 324 (located 71 bp upstream of the coding region) of the cDNA sequence shown in SEQ ID NO. 10 encoding human dystroglycan (hDG) involved in progressive myodystrophy, and the 3' primer corresponds to positions 3164 to 3194 (located 85 bp downstream of the coding region) of the same cDNA sequence.

A PCR reaction solution was prepared as follows.

| Aqueous CDNA solution | 9.5 μl |
|---|---|
| 10 × LA PCR Buffer (Takara) | 1.25 μl |
| dNTP mix (2.5 mM each; Takara) | 1.25 μl |
| 5' primer (10 μM) | 0.125 μl |
| 3' primer (10 μM) | 0.125 μl |
| PerfectMatch (Stratagene) | 0.125 μl |
| Total | 12.375 μl |

The reaction solution described above was incubated at 94° C. for 2 min and then 0.125 μl of LA Taq polymerase (Takara) was added thereto (to make the total volume 12.5 μl). A PCR was performed in Thermal Cycler 480 (Perkin Elmer Cetus) for 35 cycles (94 ° C. for 1 min, 65° C. for 1 min and 72 ° C. for 3 min). Thereafter, the resultant solution was reacted further at 72° C. for 10 min.

Figure 3:
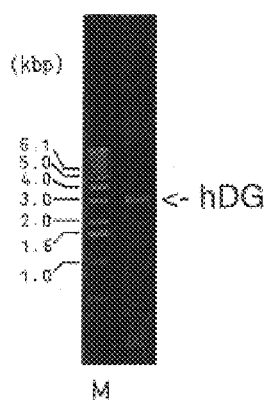
FIG. 3 is a photograph showing the results of agarose gel electrophoresis for dystroglycan.

The amplified product was subjected to agarose gel electrophoresis. As a result, it was found that a cDNA coding for hDG (a 2901 bp cDNA fragment corresponding to positions 294 to 3194 of the base sequence shown in SEQ ID NO. 10) has been amplified (FIG. 3, the right lane). In FIG. 3, the left lane (M) represents molecular markers.

In this Example, a cDNA of approximately 3 kb could be amplified.

Thus, it has become clear that the method of the present invention can amplify a cDNA of an extremely small quantity and also that the method of the invention is not subject to limitations from the size of a target cDNA.

Example 2

Amplification of a cDNA Encoding Human α-Sarcoglycan (hα-SG) which is One of the Candidate Proteins Involved in Progressive Muscular Dystrophy In order to amplify a cDNA encoding human α-sarcoglycan (hα-SG) as a target cDNA, total RNA was prepared from peripheral blood and cDNA synthesis and PCR were performed in the same manner as in Example 1.

Primer for cDNA synthesis hα-SGP: SEQ ID NO. 4

5' Primer hα-SGU for PCR: SEQ ID NO. 5

3' Primer hα-SGL for PCR: SEQ ID NO. 6

The sequences shown in SEQ ID NOS. 4, 5 and 6 correspond to partial sequences of the cDNA sequence encoding hα-SG (shown in SEQ ID NO. 11). SEQ ID NO. 4 corresponds to positions 1325 to 1349 (located 121 bp downstream of the coding region); SEQ ID NO. 5 corresponds to positions 1 to 21 (located 23 bp upstream of the coding region); and SEQ ID NO. 6 corresponds to positions 1216 to 1236 (located 12 bp downstream of the coding region).

A PCR was performed for 35 cycles (94° C. for 1 min, 55° C. for 1 min and 72° C. for 1.5 min). Thereafter, the reaction solution was reacted further at 72° C. for 10 min.

Figure 4:
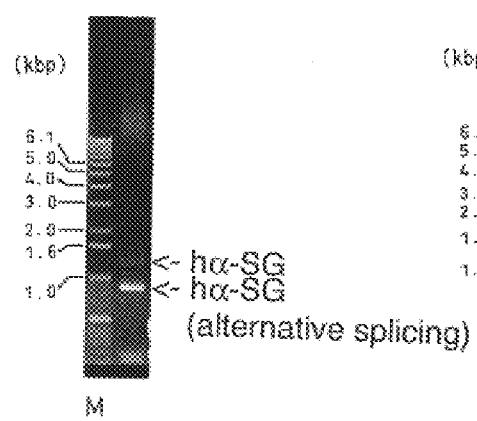
FIG. 4 is a photograph showing the results of agarose gel electrophoresis for α-sarcoglycan.

The amplified product was subjected to agarose gel electrophoresis. As a result, it was found that two cDNA fragments have been amplified. One has a 1236 bp base sequence corresponding to positions 1 to 1236 of SEQ ID NO. 11 and the other has a 864 bp base sequence corresponding to positions 1 to 864 of SEQ ID NO. 12 (FIG. 4, the right lane).

It is known that the genomic DNA fragment encoding hα-SG undergoes the so-called "selective splicing" to produce two gene products (E. M. McNally et al., Proc. Natl. Acad. Sci. USA, 91, 9690–9694 (1994)). Selective splicing is a mechanism in which multiple isotype mRNAs are generated from one gene. Due to this mechanism, a mature transcript lacking a certain exon is generated during the processing of transcripts of a gene. The two cDNA molecules of 1236 bp and 864 bp described above have been generated because selective splicing occurred. The base sequence shown in SEQ ID NO. 12 is a sequence derived from the base sequence shown in SEQ ID NO. 11 when a partial sequence from positions 623 to 994 has been lost due to selective splicing.

In the present invention, both of the gene products could have been isolated and identified. The method of the invention can not only amplify a gene product present in an extremely small quantity but also detect products of a gene which undergoes selective splicing.

Example 3

Amplification of a cDNA Encoding Human Endothelin B Receptor (hET$_B$) which is One of the Candidate Proteins Involved in Hirschsprung's Disease In order to amplify a cDNA encoding endothelin B receptor as a target cDNA, total RNA was prepared from peripheral blood and cDNA synthesis and PCR were performed in the same manner as in Example 1.

Primer for cDNA synthesis hETBP: SEQ ID NO. 7

5' Primer hETBU for PCR: SEQ ID NO. 8

3' Primer hETBL for PCR: SEQ ID NO. 9

The sequences shown in SEQ ID NOS. 7, 8 and 9 correspond to partial sequences of the cDNA sequence encoding hETB (shown in SEQ ID NO. 13). SEQ ID NO. 7 corresponds to positions 1715 to 1739 (located 159 bp downstream of the coding region); SEQ ID NO. 8 corresponds to positions 170 to 191 (located 40 bp upstream of the coding region); and SEQ ID NO. 9 corresponds to positions 1594 to 1615 (located 38 bp downstream of the coding region).

A PCR was performed for 40 cycles (94° C. for 1 min, 45° C. for 1 min and 72° C. for 1.5 min). Thereafter, the reaction solution was reacted further at 72° C. for 10 min. The cDNA used in the PCR was prepared from an RNA/cDNA hybrid by degrading the RNA with alkali and then adsorption-purifying the cDNA with glass beads.

Figure 5:
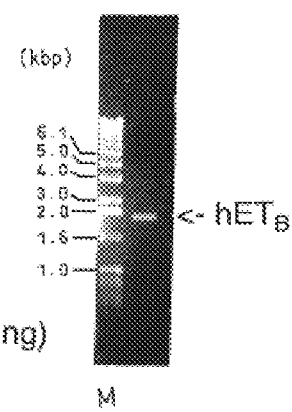
FIG. 5 is a photograph showing the results of agarose gel electrophoresis for endothelin B receptor.

The amplified product was subjected to agarose gel electrophoresis. As a result, it was found that a cDNA encoding hETB (a 1446 bp cDNA fragment corresponding to positions 170 to 1615 of the base sequence shown in SEQ ID NO. 13) has been amplified (FIG. 5, the right lane).

In order to amplify a target cDNA, a small amount of blood (usually, 1 ml of peripheral blood) will be sufficient. In the Examples of the present invention, however, the amplification of a target cDNA has been secured by increasing the amount of blood to 3 ml (which is still a small amount). In the Examples, even when the amount of an mRNA "leaking out" to the peripheral blood leukocyte was extremely small, it was possible to detect the mRNA by increasing the amount of blood sample and purifying the cDNA template without non-specific amplification of the cDNA even under increased PCR cycles.

According to the present invention, it is possible to amplify a cDNA encoding the entire coding region of a target mRNA expressed only in an extremely small amount by performing one PCR. Accordingly, with the present invention, it is possible to perform a practical and rapid screening of a candidate causative gene for various inherited diseases or cancers.

The method of the invention is particularly useful in searching for variation in base sequences in an mRNA expressed only in brain where biopsy is extremely difficult from an ethical viewpoint in cases of, for example, dementia which will become a serious issue in the aged society to come.

In addition, the amount of peripheral blood needed in the present invention for amplifying a cDNA from a tissue-specific mRNA is as small as a few milliliters. Therefore, a blood sample collected for the routine blood examination in hospitals or even the remainder of such a sample will be sufficient for the method of the invention. Thus, the method of the invention does not give a special pain to patients.

EFFECT OF THE INVENTION

According to the present invention, a method for specifically amplifying a cDNA synthesized from an mRNA expressed only in an extremely small quantity is provided.

What is claimed is:

1. A method for detecting a tissue specific cDNA having a coding region which is not actively transcribed in peripheral blood comprising:

synthesizing the tissue specific cDNA from a target mRNA in the peripheral blood using an oligonucleotide primer shown in SEQ ID NO: 1, wherein the tissue specific cDNA encodes dystroglycan and has a base sequence shown in SEQ ID NO: 10 or a fragment thereof;

amplifying the coding region of the resultant cDNA by only one round of PCR using a 5' primer and a 3' primer each having 20–40 bases, wherein the 3' primer is located between the coding region and the oligonucleotide primer; and detecting the amplified cDNA.

2. The method of claim 1, wherein the 5' primer has the base sequence shown in SEQ ID NO:2 and the 3' primer has the base sequence shown in SEQ ID NO:3.

3. The method of claim 2, wherein the amplified cDNA is a cDNA fragment corresponding to positions 294 to 3194 of the base sequence shown in SEQ ID NO:10.

4. A method for detecting a tissue specific cDNA having a coding region which is not actively transcribed in peripheral blood comprising:

synthesizing the tissue specific cDNA from a target mRNA in the peripheral blood using an oligonucleotide primer shown in SEQ ID NO:4, wherein the tissue specific cDNA encodes α-sarcoglycan and has a base sequence shown in SEQ ID NO: 11 or 12 or a fragment thereof;

amplifying the coding region of the resultant cDNA by only one round of PCR using a 5' primer and a 3' primer each having 20–40 bases, wherein the 3' primer is located between the coding region and the oligonucleotide primer; and detecting the amplified cDNA.

5. The method of claim 4, wherein the 5' primer has the base sequence shown in SEQ ID NO:5 and the 3' primer has the base sequence shown in SEQ ID NO:6.

6. The method of claim 5, wherein the amplified cDNA is a cDNA fragment corresponding to positions 1 to 1236 of the base sequence shown in SEQ ID NO:11, or positions 1 to 864 of the base sequence shown in SEQ ID NO:12.

7. A method for detecting a tissue specific cDNA having a coding region which is not actively transcribed in peripheral blood comprising:

synthesizing the tissue specific cDNA from a target mRNA in the peripheral blood using an oligonucleotide primer sequence shown in SEQ ID NO:7, wherein the tissue specific cDNA encodes endothelin B receptor and has a base sequence shown in SEQ ID NO: 13 or a fragment thereof;

amplifying the coding region of the resultant cDNA by only one round of PCR using a 5' primer and a 3' primer each having 20–40 bases, wherein the 3' primer is located between the coding region and the oligonucleotide primer; and detecting the amplified cDNA.

8. The method of claim 7, wherein the 5' primer has the base sequence shown in SEQ ID NO:8 and the 3' primer has the base sequence shown in SEQ ID NO:9.

9. The method of claim 8, wherein the amplified cDNA is a cDNA fragment corresponding to positions 170 to 1615 of the base sequence shown in SEQ ID NO:13.

10. A kit for detecting a cDNA encoding dystroglycan in peripheral blood comprising a set of oligonucleotide primers having the base sequence shown in SEQ ID NO:1 for cDNA synthesis and SEQ ID NOS:2 and 3 for PCR.

11. A kit for detecting a cDNA encoding α-sarcoglycan in peripheral blood comprising a set of oligonucleotide primers having the base sequence shown in SEQ ID NO:4 for cDNA synthesis and SEQ ID NOS:5 and 6 for PCR.

12. A kit for detecting a cDNA encoding human endothelin B receptor in peripheral blood comprising a set of oligonucleotide primers having the base sequence shown in SEQ ID NO:7 for cDNA synthesis and SEQ ID NOS:8 and 9 for PCR.

* * * * *

```
                          SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 1:

TTGTCCAGGC CCCTGTGTCA GTGTG                                           25

(2) INFORMATION FOR SEQ ID NO: 2:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 2:

GGATGGAGCA GGTGTGCAGA GGGTGAGAAC C                                    31

(2) INFORMATION FOR SEQ ID NO: 3:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 3:

TCAGGTGTCG GCTCCCGGTG GGCAATGGTC T                                    31

(2) INFORMATION FOR SEQ ID NO: 4:

(i) SEQUENCE CHARACTERISTICS:
       (A) LENGTH: 25 base pairs
```

```
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 4:

CCACCCCCTC TCCCTGCTTG TTTAG                                             25

(2) INFORMATION FOR SEQ ID NO: 5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 5:

CCCCTGTCTC TGTCACTCAC C                                                 21

(2) INFORMATION FOR SEQ ID NO: 6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 6:

GGCTGGACCT GGAACCACTG G                                                 21

(2) INFORMATION FOR SEQ ID NO: 7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 7:

CCGTAAACAG CTCATAAAAT GTCAT                                             25

(2) INFORMATION FOR SEQ ID NO: 8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 8:

TTGTCTCTAG GCTCTGAAAC TG                                                22

(2) INFORMATION FOR SEQ ID NO: 9:

(i) SEQUENCE CHARACTERISTICS:
```

```
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "synthetic DNA"

(xi) SEQUENCE DESCRIPTION: SEQ ID NO: 9:

TTTTAATGAC TTCGGTCCAA TA                                              22

(2) INFORMATION FOR SEQ ID NO: 10:

(i) SEQUENCE CHARACTERISTICS:
        (A) LENGTH: 5494 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION:395..3079

(xi) SEQUENCE DESCRIPTION: SEQ ID NO: 10:

GGGCCAGTCG GCGCCGCGCG GAGCTGGCCG CTGGATTGGC TGCAACACTC GCGTGTCAGG        60

CGGTTGCTAG GCTCCGGCCG CGCGCCCCGC CCTTGCGCTC AGCGCCCTCT CACCGCCCGG       120

TACGTGCTCG CGCGAAGGCT GCGGCGCGGC GCTCGCGCCT CTTAGGCTTG GCGGTGGCGG       180

CGGCGGCAGC TTCGCGCCGA ATCCCCGGGG AGCGGCGGTG GCGGCGTCCT GGGGCCAGGA       240

GGAGCGAACA CCTGCCGCGG TCCTCCCGCC GGCGCTGGGC TCTGTGTGCT CCGGGATGGA       300

GCAGGTGTGC AGAGGGTGAG AACCCAGCTC TGGGACCAAG TCACTTGCTT CCTTACTTAG       360

CAAGACTATC GACTTGAGCA AACTTGGACC TGGG ATG AGG ATG TCT GTG GGC          412
                                  Met Arg Met Ser Val Gly
                                    1               5

CTC TCG CTG CTG CTG CCC CTC TGG GGG AGG ACC TTT CTC CTC CTG CTC        460
Leu Ser Leu Leu Leu Pro Leu Trp Gly Arg Thr Phe Leu Leu Leu Leu
                 10                  15                  20

TCT GTG GTT ATG GCT CAG TCC CAC TGG CCC AGT GAA CCC TCA GAG GCT        508
Ser Val Val Met Ala Gln Ser His Trp Pro Ser Glu Pro Ser Glu Ala
             25                  30                  35

GTC AGG GAC TGG GAA AAC CAG CTT GAG GCA TCC ATG CAC TCA GTG CTC        556
Val Arg Asp Trp Glu Asn Gln Leu Glu Ala Ser Met His Ser Val Leu
         40                  45                  50

TCA GAC CTC CAC GAG GCT GTT CCC ACA GTG GTT GGC ATT CCT GAT GGC        604
Ser Asp Leu His Glu Ala Val Pro Thr Val Val Gly Ile Pro Asp Gly
 55                  60                  65                  70

ACG GCT GTC GTC GGG CGC TCA TTT CGA GTG ACC ATT CCA ACA GAT TTG        652
Thr Ala Val Val Gly Arg Ser Phe Arg Val Thr Ile Pro Thr Asp Leu
                 75                  80                  85

ATT GCC TCC AGT GGA GAT ATC ATC AAG GTA TCA GCG GCA GGG AAG GAG        700
Ile Ala Ser Ser Gly Asp Ile Ile Lys Val Ser Ala Ala Gly Lys Glu
             90                  95                 100

GCT TTG CCA TCT TGG CTG CAC TGG GAC TCA CAG AGC CAC ACC CTG GAG        748
Ala Leu Pro Ser Trp Leu His Trp Asp Ser Gln Ser His Thr Leu Glu
        105                 110                 115

GGC CTC CCC CTT GAC ACT GAT AAG GGT GTG CAT TAC ATT TCA GTG AGC        796
Gly Leu Pro Leu Asp Thr Asp Lys Gly Val His Tyr Ile Ser Val Ser
    120                 125                 130

GCT ACA CGG CTG GGG GCC AAC GGG AGC CAC ATC CCC CAG ACC TCC AGT        844
Ala Thr Arg Leu Gly Ala Asn Gly Ser His Ile Pro Gln Thr Ser Ser
```

-continued

```
      135                 140                 145                 150
GTG TTC TCC ATC GAG GTC TAC CCT GAA GAC CAC AGT GAT CTG CAG TCG        892
Val Phe Ser Ile Glu Val Tyr Pro Glu Asp His Ser Asp Leu Gln Ser
                155                 160                 165

GTG AGG ACA GCC TCC CCA GAC CCT GGT GAG GTG GTA TCA TCT GCC TGT        940
Val Arg Thr Ala Ser Pro Asp Pro Gly Glu Val Val Ser Ser Ala Cys
                170                 175                 180

GCT GCG GAT GAA CCT GTG ACT GTT TTG ACG GTG ATT TTG GAT GCC GAC        988
Ala Ala Asp Glu Pro Val Thr Val Leu Thr Val Ile Leu Asp Ala Asp
                185                 190                 195

CTC ACC AAG ATG ACC CCA AAG CAA AGG ATT GAC CTC CTG CAC AGG ATG       1036
Leu Thr Lys Met Thr Pro Lys Gln Arg Ile Asp Leu Leu His Arg Met
        200                 205                 210

CGG AGC TTC TCA GAA GTA GAG CTT CAC AAC ATG AAA TTA GTG CCG GTG       1084
Arg Ser Phe Ser Glu Val Glu Leu His Asn Met Lys Leu Val Pro Val
215                 220                 225                 230

GTG AAT AAC AGA CTA TTT GAC ATG TCG GCC TTC ATG GCT GGC CCG GGA       1132
Val Asn Asn Arg Leu Phe Asp Met Ser Ala Phe Met Ala Gly Pro Gly
                235                 240                 245

AAT CCA AAA AAG GTG GTG GAG AAT GGG GCC CTT CTC TCC TGG AAG CTG       1180
Asn Pro Lys Lys Val Val Glu Asn Gly Ala Leu Leu Ser Trp Lys Leu
                250                 255                 260

GGC TGC TCC CTG AAC CAG AAC AGT GTG CCT GAC ATT CAT GGT GTA GAG       1228
Gly Cys Ser Leu Asn Gln Asn Ser Val Pro Asp Ile His Gly Val Glu
        265                 270                 275

GCC CCT GCC AGG GAG GGC GCA ATG TCT GCT CAG CTT GGC TAC CCT GTG       1276
Ala Pro Ala Arg Glu Gly Ala Met Ser Ala Gln Leu Gly Tyr Pro Val
        280                 285                 290

GTG GGT TGG CAC ATC GCC AAT AAG AAG CCC CCT CTT CCC AAA CGC GTC       1324
Val Gly Trp His Ile Ala Asn Lys Lys Pro Pro Leu Pro Lys Arg Val
295                 300                 305                 310

CGG AGG CAG ATC CAT GCT ACA CCC ACA CCT GTC ACT GCC ATT GGG CCC       1372
Arg Arg Gln Ile His Ala Thr Pro Thr Pro Val Thr Ala Ile Gly Pro
                315                 320                 325

CCA ACC ACG GCT ATC CAG GAG CCC CCA TCC AGG ATC GTG CCA ACC CCC       1420
Pro Thr Thr Ala Ile Gln Glu Pro Pro Ser Arg Ile Val Pro Thr Pro
                330                 335                 340

ACA TCT CCA GCC ATT GCT CCT CCA ACA GAG ACC ATG GCT CCT CCA GTC       1468
Thr Ser Pro Ala Ile Ala Pro Pro Thr Glu Thr Met Ala Pro Pro Val
        345                 350                 355

AGG GAT CCT GTT CCT GGG AAA CCC ACG GTC ACC ATC CGG ACT CGA GGC       1516
Arg Asp Pro Val Pro Gly Lys Pro Thr Val Thr Ile Arg Thr Arg Gly
        360                 365                 370

GCC ATT ATT CAA ACC CCA ACC CTA GGC CCC ATC CAG CCT ACT CGG GTG       1564
Ala Ile Ile Gln Thr Pro Thr Leu Gly Pro Ile Gln Pro Thr Arg Val
375                 380                 385                 390

TCA GAA GCT GGC ACC ACA GTT CCT GGC CAG ATT CGC CCA ACG ATG ACC       1612
Ser Glu Ala Gly Thr Thr Val Pro Gly Gln Ile Arg Pro Thr Met Thr
                395                 400                 405

ATT CCT GGC TAT GTG GAG CCT ACT GCA GTT GCT ACC CCT CCA ACA ACC       1660
Ile Pro Gly Tyr Val Glu Pro Thr Ala Val Ala Thr Pro Pro Thr Thr
                410                 415                 420

ACC ACC AAG AAG CCA CGA GTA TCC ACA CCA AAA CCA GCA ACG CCT TCA       1708
Thr Thr Lys Lys Pro Arg Val Ser Thr Pro Lys Pro Ala Thr Pro Ser
        425                 430                 435

ACT GAC TCC ACC ACC ACC ACG ACT CGC AGG CCA ACC AAG AAA CCA CGG       1756
Thr Asp Ser Thr Thr Thr Thr Thr Arg Arg Pro Thr Lys Lys Pro Arg
        440                 445                 450

ACA CCC CGG CCA GTG CCC CGG GTC ACC ACC AAA GTT TCC ATC ACC AGA       1804
```

```
Thr Pro Arg Pro Val Pro Arg Val Thr Thr Lys Val Ser Ile Thr Arg
455                 460                 465                 470

TTG GAA ACT GCC TCA CCG CCT ACT CGT ATT CGC ACC ACC ACC AGT GGA      1852
Leu Glu Thr Ala Ser Pro Pro Thr Arg Ile Arg Thr Thr Thr Ser Gly
                475                 480                 485

GTG CCC CGT GGC GGA GAA CCC AAC CAG CGC CCA GAG CTC AAG AAC CAT      1900
Val Pro Arg Gly Gly Glu Pro Asn Gln Arg Pro Glu Leu Lys Asn His
            490                 495                 500

ATT GAC AGG GTA GAT GCC TGG GTT GGC ACC TAC TTT GAG GTG AAG ATC      1948
Ile Asp Arg Val Asp Ala Trp Val Gly Thr Tyr Phe Glu Val Lys Ile
                505                 510                 515

CCG TCA GAC ACT TTC TAT GAC CAT GAG GAC ACC ACC ACT GAC AAG CTG      1996
Pro Ser Asp Thr Phe Tyr Asp His Glu Asp Thr Thr Thr Asp Lys Leu
        520                 525                 530

AAG CTG ACC CTG AAA CTG CGG GAG CAG CAG CTG GTG GGC GAG AAG TCC      2044
Lys Leu Thr Leu Lys Leu Arg Glu Gln Gln Leu Val Gly Glu Lys Ser
535                 540                 545                 550

TGG GTA CAG TTC AAC AGC AAC AGC CAG CTC ATG TAT GGC CTT CCC GAC      2092
Trp Val Gln Phe Asn Ser Asn Ser Gln Leu Met Tyr Gly Leu Pro Asp
                555                 560                 565

AGC AGC CAC GTG GGC AAA CAC GAG TAT TTC ATG CAT GCC ACA GAC AAG      2140
Ser Ser His Val Gly Lys His Glu Tyr Phe Met His Ala Thr Asp Lys
            570                 575                 580

GGG GGC CTG TCG GCT GTG GAT GCC TTC GAG ATC CAC GTC CAC AGG CGC      2188
Gly Gly Leu Ser Ala Val Asp Ala Phe Glu Ile His Val His Arg Arg
                585                 590                 595

CCC CAA GGG GAT AGG GCT CCT GCA AGG TTC AAG GCC AAG TTT GTG GGT      2236
Pro Gln Gly Asp Arg Ala Pro Ala Arg Phe Lys Ala Lys Phe Val Gly
        600                 605                 610

GAC CCG GCA CTG GTG TTG AAT GAC ATC CAC AAG AAG ATT GCC TTG GTA      2284
Asp Pro Ala Leu Val Leu Asn Asp Ile His Lys Lys Ile Ala Leu Val
615                 620                 625                 630

AAG AAA CTG GCC TTC GCC TTT GGA GAC CGA AAC TGT AGC ACC ATC ACC      2332
Lys Lys Leu Ala Phe Ala Phe Gly Asp Arg Asn Cys Ser Thr Ile Thr
                635                 640                 645

CTG CAG AAT ATC ACC CGG GGC TCC ATC GTG GTG GAA TGG ACC AAC AAC      2380
Leu Gln Asn Ile Thr Arg Gly Ser Ile Val Val Glu Trp Thr Asn Asn
            650                 655                 660

ACA CTG CCC TTG GAG CCC TGC CCC AAG GAG CAG ATC GCT GGG CTG AGC      2428
Thr Leu Pro Leu Glu Pro Cys Pro Lys Glu Gln Ile Ala Gly Leu Ser
        665                 670                 675

CGC CGG ATC GCT GAG GAT GAT GGA AAA CCT CGG CCT GCC TTC TCC AAC      2476
Arg Arg Ile Ala Glu Asp Asp Gly Lys Pro Arg Pro Ala Phe Ser Asn
680                 685                 690

GCC CTA GAG CCT GAC TTT AAG GCC ACA AGC ATC ACT GTG ACG GGC TCT      2524
Ala Leu Glu Pro Asp Phe Lys Ala Thr Ser Ile Thr Val Thr Gly Ser
695                 700                 705                 710

GGC AGT TGT CGG CAC CTA CAG TTT ATC CCT GTG GTA CCA CCC AGG AGA      2572
Gly Ser Cys Arg His Leu Gln Phe Ile Pro Val Val Pro Pro Arg Arg
                715                 720                 725

GTG CCC TCA GAG GCG CCG CCC ACA GAA GTG CCT GAC AGG GAC CCT GAG      2620
Val Pro Ser Glu Ala Pro Pro Thr Glu Val Pro Asp Arg Asp Pro Glu
            730                 735                 740

AAG AGC AGT GAG GAT GAT GTC TAC CTG CAC ACA GTC ATT CCG GCC GTG      2668
Lys Ser Ser Glu Asp Asp Val Tyr Leu His Thr Val Ile Pro Ala Val
                745                 750                 755

GTG GTC GCA GCC ATC CTG CTC ATT GCT GGC ATC ATT GCC ATG ATC TGC      2716
Val Val Ala Ala Ile Leu Leu Ile Ala Gly Ile Ile Ala Met Ile Cys
        760                 765                 770
```

```
TAC CGC AAG AAG CGG AAG GGC AAG CTT ACC CTT GAG GAC CAG GCC ACC        2764
Tyr Arg Lys Lys Arg Lys Gly Lys Leu Thr Leu Glu Asp Gln Ala Thr
775             780                 785                 790

TTC ATC AAG AAG GGG GTG CCT ATC ATC TTT GCA GAC GAA CTG GAC GAC        2812
Phe Ile Lys Lys Gly Val Pro Ile Ile Phe Ala Asp Glu Leu Asp Asp
                795                 800                 805

TCC AAG CCC CCA CCC TCC TCC AGC ATG CCA CTC ATT CTG CAG GAG GAG        2860
Ser Lys Pro Pro Pro Ser Ser Ser Met Pro Leu Ile Leu Gln Glu Glu
            810                 815                 820

AAG GCT CCC CTA CCC CCT CCT GAG TAC CCC AAC CAG AGT GTG CCC GAG        2908
Lys Ala Pro Leu Pro Pro Pro Glu Tyr Pro Asn Gln Ser Val Pro Glu
        825                 830                 835

ACC ACT CCT CTG AAC CAG GAC ACC ATG GGA GAG TAC ACG CCC CTG CGG        2956
Thr Thr Pro Leu Asn Gln Asp Thr Met Gly Glu Tyr Thr Pro Leu Arg
    840                 845                 850

GAT GAG GAT CCC AAT GCG CCT CCC TAC CAG CCC CCA CCG CCC TTC ACA        3004
Asp Glu Asp Pro Asn Ala Pro Pro Tyr Gln Pro Pro Pro Pro Phe Thr
855                 860                 865                 870

GTA CCC ATG GAG GGC AAG GGC TCC CGT CCC AAG AAC ATG ACC CCA TAC        3052
Val Pro Met Glu Gly Lys Gly Ser Arg Pro Lys Asn Met Thr Pro Tyr
                875                 880                 885

CGG TCA CCT CCT CCC TAT GTC CCA CCT TAACCCGCAA GCGCCTGGGT              3099
Arg Ser Pro Pro Pro Tyr Val Pro Pro
            890                 895

GGAGGCAGGG TAGGGCAGGG CCCTGGAGAC GACATGGTGT TGTCTGTGGA GACCGGTGGC      3159
CTGCAGACCA TTGCCCACCG GGAGCCGACA CCTGACCTAG CACACACTGA CACAGGGGCC      3219
TGGACAAGCC CGCCCTCTCT GGTCCTCCCA AACCCCAAAG CAGCTGGAGA GACTTTGGGG      3279
ACTTTTTTAT TTTTATTTTT TGCCTAACAG CTTTTGGTTT GTTCATAGAG AACTCTTCGC      3339
TTCATTTTTG ATGGCTGGCT CTGAAAGCAC CATGTGGAGT GGAGGTGGAG GGACCGAGGA      3399
ACCATGAATG AACTCGCAGG CAGTGCCGGG CGGCCCCCTG GCTCTCTGCG TTTTGCCTTT      3459
AACACTAACT GTACTGTTTT TTCTATTCAC GTGTGTCTAG CTGCAGGATG TAACATGGAA      3519
AACAGTAACT AAAGATTAAA TTCAAAGGAC TTTCAGAAGT TAAGGTTAAG TTTTTACGTT      3579
TAATCTGCTG TTTACCTAAA CTTGTATGTA TAATTTTTGG GTGGGTATGG GGAATTGCTT      3639
TGCTAAAAAT AAGCTCCCAG GGTGTTTCAA ACTTAGAGAA GACCAAGGGA CAGTATTTTT      3699
TATCAAAGGA ATACTATTTT TTCACACTAC GTCAACTTGG TTGCTCTGAT ACCCCAGAGC      3759
CTGATTGGGG GCCTCCCGGC CCTGGCTCAC GCCAAGTCCC TGGTGCTGGG TTTGCTCTCC      3819
CGCTGTTGCC AGGGGCTGGA AGCTGGAGGG GTCTCTTGGG CCATGGACAT CCCCACTTCC      3879
AGCCCATGTA CACTAGTGGC CCACGACCAA GGGGTCTTCA TTTCCATGAA AAAGGGACTC      3939
CAAGAGGCAG TGGTGGCTGT GGCCCCCAAC TTTGGTGCTC CAGGGTGGGC CAACTGCTTG      3999
TGGGGGCACC TGGAGGTCA AAGGTCTCCA CCACATCAAC CTATTTTGTT TTACCCTTTT       4059
TCTGTGCATT GTTTTTTTTT TTCCTCCTAA AAGGAATATC ACGGTTTTTT GAAACACTCA      4119
GTGGGGACA TTTTGGTGAA GATGCAATAT TTTTATGTCA TGTGATGCTC TTTCCTCACT       4179
TGACCTTGGC CGCTTTGTCC TAACAGTCCA CAGTCCTGCC CCGACCCACC CCATCCCTTT     4239
TCTCTGGCAC TCCAGTCCAG CTTGGGCCTG AACTACTGGA AAAGGTCTGG CGGCTGGGGA     4299
GGAGTGCCAG CAATAGTTCA TAATAAAAAT CTGTTAGCTC TCAAAGCTAA TTTTTTACTA    4359
AAGTTTTTAT ACAGCTCAA ATTGTTTTAT TAAAAAAAG ATTTAAAATG GTGATGCTTA       4419
CAGCAGTTTG TACGAGCTCT TAAGTGTTGA TTCCATGGAA CTGACGGCTT TGCTTGTTTT     4479
GATTCTTTTC CCCCTACTTT TCCTAATGGT TTAAATTCTG GAATTACACT GGGGTTCTTT    4539
```

-continued

```
TGCCTTTTTT AGCAGAACAT CCGTCCGTCC ATCTGCATCT CTGTCCCATG ACTCAGGGGC      4599

GCCCACTCTG CTTCGATTCT CCTCCTGTGG AAGAAACCAT TTTGAGCATG ACTTTTCTTG      4659

ATGTCTGAAG CGTTATTTTG GGTACTTTTT AGGGAGGAAT GCCTTTCGCA ATAATGTATC      4719

CATTCCCCTG ATTGAGGGTG GGTGGGTGGA CCCAGGCTCC CTTTGCACAC AGAGCAGCTA      4779

CTTCTAAGCC ATATCGACTG TTTTGCAGAG GATTTGTGTG TCCTCCCTCA GGAGGGGAGG      4839

CCTGGTAGGA GGGGGGGAGA GTTCTCTGTC CTACTGCTCT CAAGAGGGCA TTTCCCCTTG      4899

CGCCTTCTCC CACAGGGCCC AGCCCCTCTC CCCTGCCCAA GTCCCAGGG GGTACTCTGG       4959

AGTGAGCAGT CCCCCTGTGG GGGAGCCTGT AAATGCGGGC TCAGTGGACC ACTGGTGACT      5019

GGGCTCATGC CTCCAAGTCA GAGTTTCCCC TGGTGCCCCA GAGACAGGAG CACAAGTGGG      5079

ATCTGACCTG GTGAGATTAT TTCTGATGAC CTCATCAAAA AATAAACAAT TCCCAATGTT      5139

CCAGGTGAGG GCTTTGAAAG GCCTTCCAAA CAGCTCCGTC GCCCCTAGCA ACTCCACCAT      5199

TGGGCACTGC CATGCAGAGA CGTGGCTGGC CCAGAATGGC CTGTTGCCAT AGCAACTGGA      5259

GGCGATGGGG CAGTGAACAG AATAACAACA GCAACAATGC CTTTGCAGGC AGCCTGCTCC      5319

CCTGAGCGCT GGGCTGGTGA TGGCCGTTGG ACTCTGTGAG ATGGAGAGCC AATCTCACAT      5379

TCAAGTGTTC ACCAACCACT GATGTGTTTT TATTTCCTTC TATATGATTT TAAGATGTGT      5439

TTTCTGCATT CTGTAAAGAA ACATATCAAA CTAAATAAAA GCAGTGTCTT TATTC           5494
```

(2) INFORMATION FOR SEQ ID NO: 11:

(i) SEQUENCE CHARACTERISTICS:
        (A) LENGTH: 1436 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION:44..1204

(xi) SEQUENCE DESCRIPTION: SEQ ID NO: 11:

```
CCCCTGTCTC TGTCACTCAC CGGGCGGGCC AGGCCGGGCA GCC ATG GCT GAG ACA         55
                                              Met Ala Glu Thr
                                                1

CTC TTC TGG ACT CCT CTC CTC GTG GTT CTC CTG GCA GGG CTG GGG GAC        103
Leu Phe Trp Thr Pro Leu Leu Val Val Leu Leu Ala Gly Leu Gly Asp
  5                  10                  15                  20

ACC GAG GCC CAG CAG ACC ACG CTA CAC CCA CTT GTG GGC CGT GTC TTT        151
Thr Glu Ala Gln Gln Thr Thr Leu His Pro Leu Val Gly Arg Val Phe
                 25                  30                  35

GTG CAC ACC TTG GAC CAT GAG ACG TTT CTG AGC CTT CCT GAG CAT GTC        199
Val His Thr Leu Asp His Glu Thr Phe Leu Ser Leu Pro Glu His Val
         40                  45                  50

GCT GTC CCA CCC GCT GTC CAC ATC ACC TAC CAC GCC CAC CTC CAG GGA        247
Ala Val Pro Pro Ala Val His Ile Thr Tyr His Ala His Leu Gln Gly
     55                  60                  65

CAC CCA GAC CTG CCC CGG TGG CTC CGC TAC ACC CAG CGC AGC CCC CAC        295
His Pro Asp Leu Pro Arg Trp Leu Arg Tyr Thr Gln Arg Ser Pro His
 70                  75                  80

CAC CCT GGC TTC CTC TAC GGC TCT GCC ACC CCA GAA GAT CGT GGG CTC        343
His Pro Gly Phe Leu Tyr Gly Ser Ala Thr Pro Glu Asp Arg Gly Leu
 85                  90                  95                 100

CAG GTC ATT GAG GTC ACA GCC TAC AAT CGG GAC AGC TTT GAT ACC ACT        391
```

```
                Gln Val Ile Glu Val Thr Ala Tyr Asn Arg Asp Ser Phe Asp Thr Thr
                                105                 110                 115

CGG CAG AGG CTG GTG CTG GAG ATT GGG GAC CCA GAA GGC CCC CTG CTG                  439
Arg Gln Arg Leu Val Leu Glu Ile Gly Asp Pro Glu Gly Pro Leu Leu
            120                 125                 130

CCA TAC CAA GCC GAG TTC CTG GTG CGC AGC CAC GAT GCG GAG GAG GTG                  487
Pro Tyr Gln Ala Glu Phe Leu Val Arg Ser His Asp Ala Glu Glu Val
                135                 140                 145

CTG CCC TCA ACA CCT GCC AGC CGC TTC CTC TCA GCC TTG GGG GGA CTC                  535
Leu Pro Ser Thr Pro Ala Ser Arg Phe Leu Ser Ala Leu Gly Gly Leu
            150                 155                 160

TGG GAG CCC GGA GAG CTT CAG CTG CTC AAC GTC ACC TCT GCC TTG GAC                  583
Trp Glu Pro Gly Glu Leu Gln Leu Leu Asn Val Thr Ser Ala Leu Asp
165                 170                 175                 180

CGT GGG GGC CGT GTC CCC CTT CCC ATT GAG GGC CGA AAA GAA GGG GTA                  631
Arg Gly Gly Arg Val Pro Leu Pro Ile Glu Gly Arg Lys Glu Gly Val
                185                 190                 195

TAC ATT AAG GTG GGT TCT GCC TCA CCT TTT TCT ACT TGC CTG AAG ATG                  679
Tyr Ile Lys Val Gly Ser Ala Ser Pro Phe Ser Thr Cys Leu Lys Met
            200                 205                 210

GTG GCA TCC CCC GAT AGC CAC GCC CGC TGT GCC CAG GGC CAG CCT CCA                  727
Val Ala Ser Pro Asp Ser His Ala Arg Cys Ala Gln Gly Gln Pro Pro
            215                 220                 225

CTT CTG TCT TGC TAC GAC ACC TTG GCA CCC CAC TTC CGC GTT GAC TGG                  775
Leu Leu Ser Cys Tyr Asp Thr Leu Ala Pro His Phe Arg Val Asp Trp
        230                 235                 240

TGC AAT GTG ACC CTG GTG GAT AAG TCA GTG CCG GAG CCT GCA GAT GAG                  823
Cys Asn Val Thr Leu Val Asp Lys Ser Val Pro Glu Pro Ala Asp Glu
245                 250                 255                 260

GTG CCC ACC CCA GGT GAT GGG ATC CTG GAG CAT GAC CCG TTC TTC TGC                  871
Val Pro Thr Pro Gly Asp Gly Ile Leu Glu His Asp Pro Phe Phe Cys
                265                 270                 275

CCA CCC ACT GAG GCC CCA GAC CGT GAC TTC TTG GTG GAT GCT CTG GTC                  919
Pro Pro Thr Glu Ala Pro Asp Arg Asp Phe Leu Val Asp Ala Leu Val
            280                 285                 290

ACC CTC CTG GTG CCC CTG CTG GTG GCC CTG CTT CTC ACC TTG CTG CTG                  967
Thr Leu Leu Val Pro Leu Leu Val Ala Leu Leu Leu Thr Leu Leu Leu
            295                 300                 305

GCC TAT GTC ATG TGC TGC CGG CGG GAG GGA AGG CTG AAG AGA GAC CTG                 1015
Ala Tyr Val Met Cys Cys Arg Arg Glu Gly Arg Leu Lys Arg Asp Leu
            310                 315                 320

GCT ACC TCC GAC ATC CAG ATG GTC CAC CAC TGC ACC ATC CAC GGG AAC                 1063
Ala Thr Ser Asp Ile Gln Met Val His His Cys Thr Ile His Gly Asn
325                 330                 335                 340

ACA GAG GAG CTG CGG CAG ATG GCG GCC AGC CGC GAG GTG CCC CGG CCA                 1111
Thr Glu Glu Leu Arg Gln Met Ala Ala Ser Arg Glu Val Pro Arg Pro
                345                 350                 355

CTC TCC ACC CTG CCC ATG TTC AAT GTG CAC ACA GGT GAG CGG CTG CCT                 1159
Leu Ser Thr Leu Pro Met Phe Asn Val His Thr Gly Glu Arg Leu Pro
            360                 365                 370

CCC CGC GTG GAC AGC GCC CAG GTG CCC CTC ATT CTG GAC CAG CAC                     1204
Pro Arg Val Asp Ser Ala Gln Val Pro Leu Ile Leu Asp Gln His
            375                 380                 385

TGACAGCCCA GCCAGTGGTT CCAGGTCCAG CCCTGACTTC ATCCTCCCTT CTCTGTCCAC               1264

ACCACGAGTG GCACATCCCA CCTGCTGATT CCAGCTCCTG GCCCTCCTGG AACCCAGGCT               1324

CTAAACAAGC AGGGAGAGGG GGTGGGGTGG GGTGAGAGTG TGTGGAGTAA GGACATTCAG               1384

AATAAATATC TGCTGCTCTG CTCACCAATT GCTGCTGGCA GCCTCTCCCG TC                       1436
```

(2) INFORMATION FOR SEQ ID NO: 12:

(i) SEQUENCE CHARACTERISTICS:
        (A) LENGTH: 1064 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION:44..832

(xi) SEQUENCE DESCRIPTION: SEQ ID NO: 12:

```
CCCCTGTCTC TGTCACTCAC CGGGCGGGCC AGGCCGGGCA GCC ATG GCT GAG ACA         55
                                              Met Ala Glu Thr
                                                1

CTC TTC TGG ACT CCT CTC CTC GTG GTT CTC CTG GCA GGG CTG GGG GAC        103
Leu Phe Trp Thr Pro Leu Leu Val Val Leu Leu Ala Gly Leu Gly Asp
  5              10                  15                      20

ACC GAG GCC CAG CAG ACC ACG CTA CAC CCA CTT GTG GGC CGT GTC TTT        151
Thr Glu Ala Gln Gln Thr Thr Leu His Pro Leu Val Gly Arg Val Phe
                  25                  30                  35

GTG CAC ACC TTG GAC CAT GAG ACG TTT CTG AGC CTT CCT GAG CAT GTC        199
Val His Thr Leu Asp His Glu Thr Phe Leu Ser Leu Pro Glu His Val
              40                  45                  50

GCT GTC CCA CCC GCT GTC CAC ATC ACC TAC CAC GCC CAC CTC CAG GGA        247
Ala Val Pro Pro Ala Val His Ile Thr Tyr His Ala His Leu Gln Gly
          55                  60                  65

CAC CCA GAC CTG CCC CGG TGG CTC CGC TAC ACC CAG CGC AGC CCC CAC        295
His Pro Asp Leu Pro Arg Trp Leu Arg Tyr Thr Gln Arg Ser Pro His
 70                  75                  80

CAC CCT GGC TTC CTC TAC GGC TCT GCC ACC CCA GAA GAT CGT GGG CTC        343
His Pro Gly Phe Leu Tyr Gly Ser Ala Thr Pro Glu Asp Arg Gly Leu
 85                  90                  95                 100

CAG GTC ATT GAG GTC ACA GCC TAC AAT CGG GAC AGC TTT GAT ACC ACT        391
Gln Val Ile Glu Val Thr Ala Tyr Asn Arg Asp Ser Phe Asp Thr Thr
                 105                 110                 115

CGG CAG AGG CTG GTG CTG GAG ATT GGG GAC CCA GAA GGC CCC CTG CTG        439
Arg Gln Arg Leu Val Leu Glu Ile Gly Asp Pro Glu Gly Pro Leu Leu
             120                 125                 130

CCA TAC CAA GCC GAG TTC CTG GTG CGC AGC CAC GAT GCG GAG GAG GTG        487
Pro Tyr Gln Ala Glu Phe Leu Val Arg Ser His Asp Ala Glu Glu Val
         135                 140                 145

CTG CCC TCA ACA CCT GCC AGC CGC TTC CTC TCA GCC TTG GGG GGA CTC        535
Leu Pro Ser Thr Pro Ala Ser Arg Phe Leu Ser Ala Leu Gly Gly Leu
     150                 155                 160

TGG GAG CCC GGA GAG CTT CAG CTG CTC AAC GTC ACC TCT GCC TTG GAC        583
Trp Glu Pro Gly Glu Leu Gln Leu Leu Asn Val Thr Ser Ala Leu Asp
165                 170                 175                 180

CGT GGG GGC CGT GTC CCC CTT CCC ATT GAG GGC CGA AAA GGA AGG CTG        631
Arg Gly Gly Arg Val Pro Leu Pro Ile Glu Gly Arg Lys Gly Arg Leu
                 185                 190                 195

AAG AGA GAC CTG GCT ACC TCC GAC ATC CAG ATG GTC CAC CAC TGC ACC        679
Lys Arg Asp Leu Ala Thr Ser Asp Ile Gln Met Val His His Cys Thr
             200                 205                 210

ATC CAC GGG AAC ACA GAG GAG CTG CGG CAG ATG GCG GCC AGC CGC GAG        727
Ile His Gly Asn Thr Glu Glu Leu Arg Gln Met Ala Ala Ser Arg Glu
         215                 220                 225

GTG CCC CGG CCA CTC TCC ACC CTG CCC ATG TTC AAT GTG CAC ACA GGT        775
Val Pro Arg Pro Leu Ser Thr Leu Pro Met Phe Asn Val His Thr Gly
```

```
            230                 235                 240
GAG CGG CTG CCT CCC CGC GTG GAC AGC GCC CAG GTG CCC CTC ATT CTG        823
Glu Arg Leu Pro Pro Arg Val Asp Ser Ala Gln Val Pro Leu Ile Leu
245                 250                 255                 260

GAC CAG CAC TGACAGCCCA GCCAGTGGTT CCAGGTCCAG CCCTGACTTC               872
Asp Gln His

ATCCTCCCTT CTCTGTCCAC ACCACGAGTG GCACATCCCA CCTGCTGATT CCAGCTCCTG     932

GCCCTCCTGG AACCCAGGCT CTAAACAAGC AGGGAGAGGG GGTGGGGTGG GGTGAGAGTG    992

TGTGGAGTAA GGACATTCAG AATAAATATC TGCTGCTCTG CTCACCAATT GCTGCTGGCA    1052

GCCTCTCCCG TC                                                         1064

(2) INFORMATION FOR SEQ ID NO: 13:

(i) SEQUENCE CHARACTERISTICS:
        (A) LENGTH: 1873 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION:231..1556

(xi) SEQUENCE DESCRIPTION: SEQ ID NO: 13:

AGGAGTTTCG ACCCGCGCTG GCGAGTCATG AGCGCCAAGT TCCCACTGG CGCGCAAACT       60

TGAGTTACTT TTGAGCGTGG ATACTGGCGA AGAGGCTGCG GGCGGTATTA GCGTTTGCAG     120

CGACTTGGCT CGGGCAGCTG ACCCAAGTGT CCTGTCTTCC TTCCTCTGCT TGTCTCTAGG    180

CTCTGAAACT GCGGAGCGGC CACCGGACGC CTTCTGGAGC AGGTAGCAGC ATG CAG        236
                                                          Met Gln
                                                          1

CCG CCT CCA AGT CTG TGC GGA CCG GCC CTG GTT GCG CTG GTT CTT GCC      284
Pro Pro Pro Ser Leu Cys Gly Pro Ala Leu Val Ala Leu Val Leu Ala
            5                   10                  15

TGC GGC CTG TCG CGG ATC TGG GGA GAG GAG AGA GGC TTC CCG CCT GAC      332
Cys Gly Leu Ser Arg Ile Trp Gly Glu Glu Arg Gly Phe Pro Pro Asp
    20                  25                  30

AGG GCC ACT CCG CTT TTG CAA ACC GCA GAG ATA ATG ACG CCA CCC ACT      380
Arg Ala Thr Pro Leu Leu Gln Thr Ala Glu Ile Met Thr Pro Pro Thr
35                  40                  45                  50

AAG ACC TTA TGG CCC AAG GGT TCC AAC GCC AGT CTG GCG CGG TCG TTG      428
Lys Thr Leu Trp Pro Lys Gly Ser Asn Ala Ser Leu Ala Arg Ser Leu
                55                  60                  65

GCA CCT GCG GAG GTG CCT AAA GGA GAC AGG ACG GCA GGA TCT CCG CCA      476
Ala Pro Ala Glu Val Pro Lys Gly Asp Arg Thr Ala Gly Ser Pro Pro
            70                  75                  80

CGC ACC ATC TCC CCT CCC CCG TGC CAA GGA CCC ATC GAG ATC AAG GAG      524
Arg Thr Ile Ser Pro Pro Pro Cys Gln Gly Pro Ile Glu Ile Lys Glu
        85                  90                  95

ACT TTC AAA TAC ATC AAC ACG GTT GTG TCC TGC CTT GTG TTC GTG CTG      572
Thr Phe Lys Tyr Ile Asn Thr Val Val Ser Cys Leu Val Phe Val Leu
    100                 105                 110

GGG ATC ATC GGG AAC TCC ACA CTT CTG AGA ATT ATC TAC AAG AAC AAG      620
Gly Ile Ile Gly Asn Ser Thr Leu Leu Arg Ile Ile Tyr Lys Asn Lys
115                 120                 125                 130

TGC ATG CGA AAC GGT CCC AAT ATT TTG ATC GCC AGC TTG GCT CTG GGA      668
Cys Met Arg Asn Gly Pro Asn Ile Leu Ile Ala Ser Leu Ala Leu Gly
                135                 140                 145
```

```
GAC CTG CTG CAC ATC GTC ATT GAC ATC CCT ATC AAT GTC TAC AAG CTG    716
Asp Leu Leu His Ile Val Ile Asp Ile Pro Ile Asn Val Tyr Lys Leu
            150                 155                 160

CTG GCA GAG GAC TGG CCA TTT GGA GCT GAG ATG TGT AAG CTG GTG CCT    764
Leu Ala Glu Asp Trp Pro Phe Gly Ala Glu Met Cys Lys Leu Val Pro
            165                 170                 175

TTC ATA CAG AAA GCC TCC GTG GGA ATC ACT GTG CTG AGT CTA TGT GCT    812
Phe Ile Gln Lys Ala Ser Val Gly Ile Thr Val Leu Ser Leu Cys Ala
            180                 185                 190

CTG AGT ATT GAC AGA TAT CGA GCT GTT GCT TCT TGG AGT AGA ATT AAA    860
Leu Ser Ile Asp Arg Tyr Arg Ala Val Ala Ser Trp Ser Arg Ile Lys
195                 200                 205                 210

GGA ATT GGG GTT CCA AAA TGG ACA GCA GTA GAA ATT GTT TTG ATT TGG    908
Gly Ile Gly Val Pro Lys Trp Thr Ala Val Glu Ile Val Leu Ile Trp
            215                 220                 225

GTG GTC TCT GTG GTT CTG GCT GTC CCT GAA GCC ATA GGT TTT GAT ATA    956
Val Val Ser Val Val Leu Ala Val Pro Glu Ala Ile Gly Phe Asp Ile
            230                 235                 240

ATT ACG ATG GAC TAC AAA GGA AGT TAT CTG CGA ATC TGC TTG CTT CAT   1004
Ile Thr Met Asp Tyr Lys Gly Ser Tyr Leu Arg Ile Cys Leu Leu His
            245                 250                 255

CCC GTT CAG AAG ACA GCT TTC ATG CAG TTT TAC AAG ACA GCA AAA GAT   1052
Pro Val Gln Lys Thr Ala Phe Met Gln Phe Tyr Lys Thr Ala Lys Asp
            260                 265                 270

TGG TGG CTA TTC AGT TTC TAT TTC TGC TTG CCA TTG GCC ATC ACT GCA   1100
Trp Trp Leu Phe Ser Phe Tyr Phe Cys Leu Pro Leu Ala Ile Thr Ala
275                 280                 285                 290

TTT TTT TAT ACA CTA ATG ACC TGT GAA ATG TTG AGA AAG AAA AGT GGC   1148
Phe Phe Tyr Thr Leu Met Thr Cys Glu Met Leu Arg Lys Lys Ser Gly
            295                 300                 305

ATG CAG ATT GCT TTA AAT GAT CAC CTA AAG CAG AGA CGG GAA GTG GCC   1196
Met Gln Ile Ala Leu Asn Asp His Leu Lys Gln Arg Arg Glu Val Ala
            310                 315                 320

AAA ACC GTC TTT TGC CTG GTC CTT GTC TTT GCC CTC TGC TGG CTT CCC   1244
Lys Thr Val Phe Cys Leu Val Leu Val Phe Ala Leu Cys Trp Leu Pro
            325                 330                 335

CTT CAC CTC AGC AGG ATT CTG AAG CTC ACT CTT TAT AAT CAG AAT GAT   1292
Leu His Leu Ser Arg Ile Leu Lys Leu Thr Leu Tyr Asn Gln Asn Asp
            340                 345                 350

CCC AAT AGA TGT GAA CTT TTG AGC TTT CTG TTG GTA TTG GAC TAT ATT   1340
Pro Asn Arg Cys Glu Leu Leu Ser Phe Leu Leu Val Leu Asp Tyr Ile
355                 360                 365                 370

GGT ATC AAC ATG GCT TCA CTG AAT TCC TGC ATT AAC CCA ATT GCT CTG   1388
Gly Ile Asn Met Ala Ser Leu Asn Ser Cys Ile Asn Pro Ile Ala Leu
            375                 380                 385

TAT TTG GTG AGC AAA AGA TTC AAA AAC TGC TTT AAG TCA TGC TTA TGC   1436
Tyr Leu Val Ser Lys Arg Phe Lys Asn Cys Phe Lys Ser Cys Leu Cys
            390                 395                 400

TGC TGG TGC CAG TCA TTT GAA GAA AAA CAG TCC TTG GAG GAA AAG CAG   1484
Cys Trp Cys Gln Ser Phe Glu Glu Lys Gln Ser Leu Glu Glu Lys Gln
            405                 410                 415

TCG TGC TTA AAG TTC AAA GCT AAT GAT CAC GGA TAT GAC AAC TTC CGT   1532
Ser Cys Leu Lys Phe Lys Ala Asn Asp His Gly Tyr Asp Asn Phe Arg
            420                 425                 430

TCC AGT AAT AAA TAC AGC TCA TCT TGAAAGAAGA ACTATTCACT GTATTTCATT  1586
Ser Ser Asn Lys Tyr Ser Ser Ser
435                 440

TTCTTTATAT TGGACCGAAG TCATTAAAAC AAAATGAAAC ATTTGCCAAA ACAAAACAAA 1646
```

-continued

| | | | | | |
|---|---|---|---|---|---|
| AAACTATGTA | TTTGCACAGC | ACACTATTAA | AATATTAAGT | GTAATTATTT | TAACACTCAC | 1706 |
| AGCTACATAT | GACATTTTAT | GAGCTGTTTA | CGGCATGGAA | AGAAAATCAG | TGGGAATTAA | 1766 |
| GAAAGCCTCG | TCGTGAAAGC | ACTTAATTTT | TTACAGTTAG | CACTTCAACA | TAGCTCTTAA | 1826 |
| CAACTTCCAG | GATATTCACA | CAACACTTAG | GCTTAAAAAT | GAGCTCA | | 1873 |